(12) United States Patent
Gerstner et al.

(10) Patent No.: US 6,927,848 B2
(45) Date of Patent: Aug. 9, 2005

(54) METHOD AND APPARATUS FOR DETECTING DEFECTS IN A CONTINUOUSLY MOVING STRIP OF TRANSPARENT MATERIAL

(75) Inventors: Klaus Gerstner, Mainz (DE); Joachim Weber, Mainz (DE)

(73) Assignee: Scott Glas, Mainz (DE)

( * ) Notice: Subject to any disclaimer, the term of this patent is extended or adjusted under 35 U.S.C. 154(b) by 269 days.

(21) Appl. No.: 10/435,952

(22) Filed: May 12, 2003

(65) Prior Publication Data

US 2003/0218743 A1 Nov. 27, 2003

(30) Foreign Application Priority Data

May 13, 2002 (DE) ......................................... 102 21 945

(51) Int. Cl.[7] .......................... G01N 21/00; G01N 21/84
(52) U.S. Cl. ..................................... 356/239.1; 356/430
(58) Field of Search ................................. 356/429–431, 356/237.1–237.3, 239.1, 239.2, 239.7, 239.8; 250/571–572, 568, 559–561

(56) References Cited

U.S. PATENT DOCUMENTS

| 3,767,306 | A | * | 10/1973 | Mast et al. .................. 356/336 |
| 4,401,893 | A | * | 8/1983 | Dehuysser .............. 250/559.49 |
| 4,402,607 | A | * | 9/1983 | McVay et al. ............... 356/338 |
| 4,715,717 | A | * | 12/1987 | Evans ......................... 356/429 |
| 5,064,280 | A | * | 11/1991 | Ringens et al. ............. 356/28.5 |
| 6,160,625 | A | * | 12/2000 | Damer et al. ................ 356/430 |
| 6,819,427 | B1 | * | 11/2004 | Subramanian et al. ...... 356/445 |

FOREIGN PATENT DOCUMENTS

| DE | 44 44 165 A1 | 6/1996 |
| DE | 695 10 976 T2 | 2/2000 |
| JP | H10-339705 | 12/1998 |
| JP | 11-337323 | * 12/1999 |

OTHER PUBLICATIONS

A. Lenhart & H. Hulsing "Particle–Detection on Glass Substrates and Thin Film Magnetic Storage Disks" IEEE Transactions on Magnetics, vol. 26, No. 1, Jan. 1990.*

* cited by examiner

Primary Examiner—Michael P. Stafira
(74) Attorney, Agent, or Firm—Michael J. Striker

(57) ABSTRACT

To detect defects in a continuously moving strip of transparent material, especially a wide thin glass strip, a narrow monochromatic light beam is guided transverse to the motion direction of the moving strip and is coupled into the moving strip, preferably through an edge region of the moving strip, by a transparent liquid arranged between the moving strip and the light source producing the monochromatic light beam. In a first embodiment the monochromatic light beam is inclined to an upper surface of the moving strip through which it passes and is coupled into the moving strip by a transparent liquid whose index of refraction is greater than that of the atmosphere surrounding the moving strip. In a second embodiment the monochromatic light beam is parallel to the upper surface of the strip and is coupled into an edge surface of the continuously moving strip by a transparent liquid whose index of refraction is about equal to that of the moving material. In the first embodiment the light guide system for the light beam includes a prism, whose light outlet surface is parallel to the upper surface of the glass strip. The transparent liquid is arranged between the prism and the glass strip, which is supported on rolls.

32 Claims, 3 Drawing Sheets

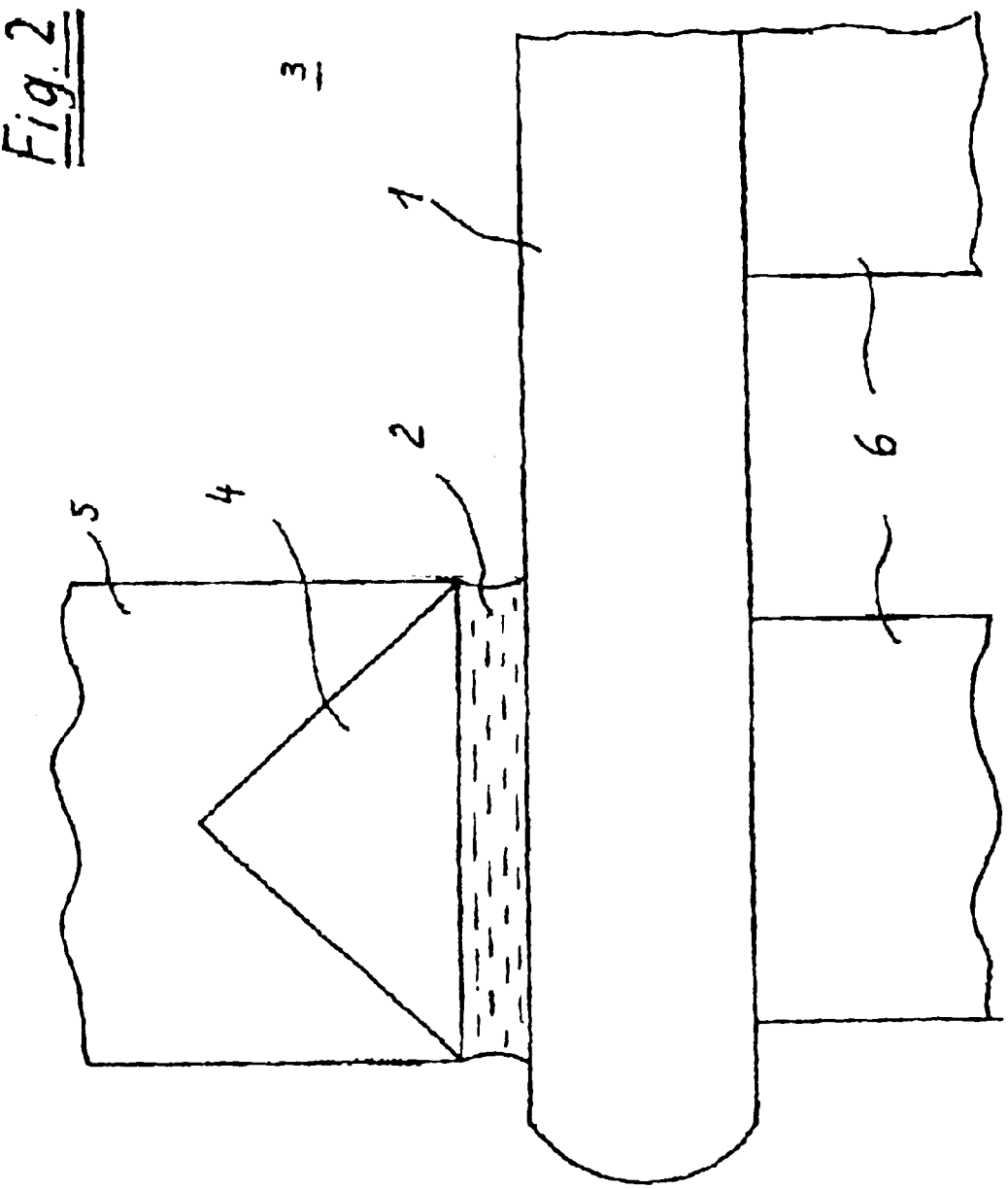

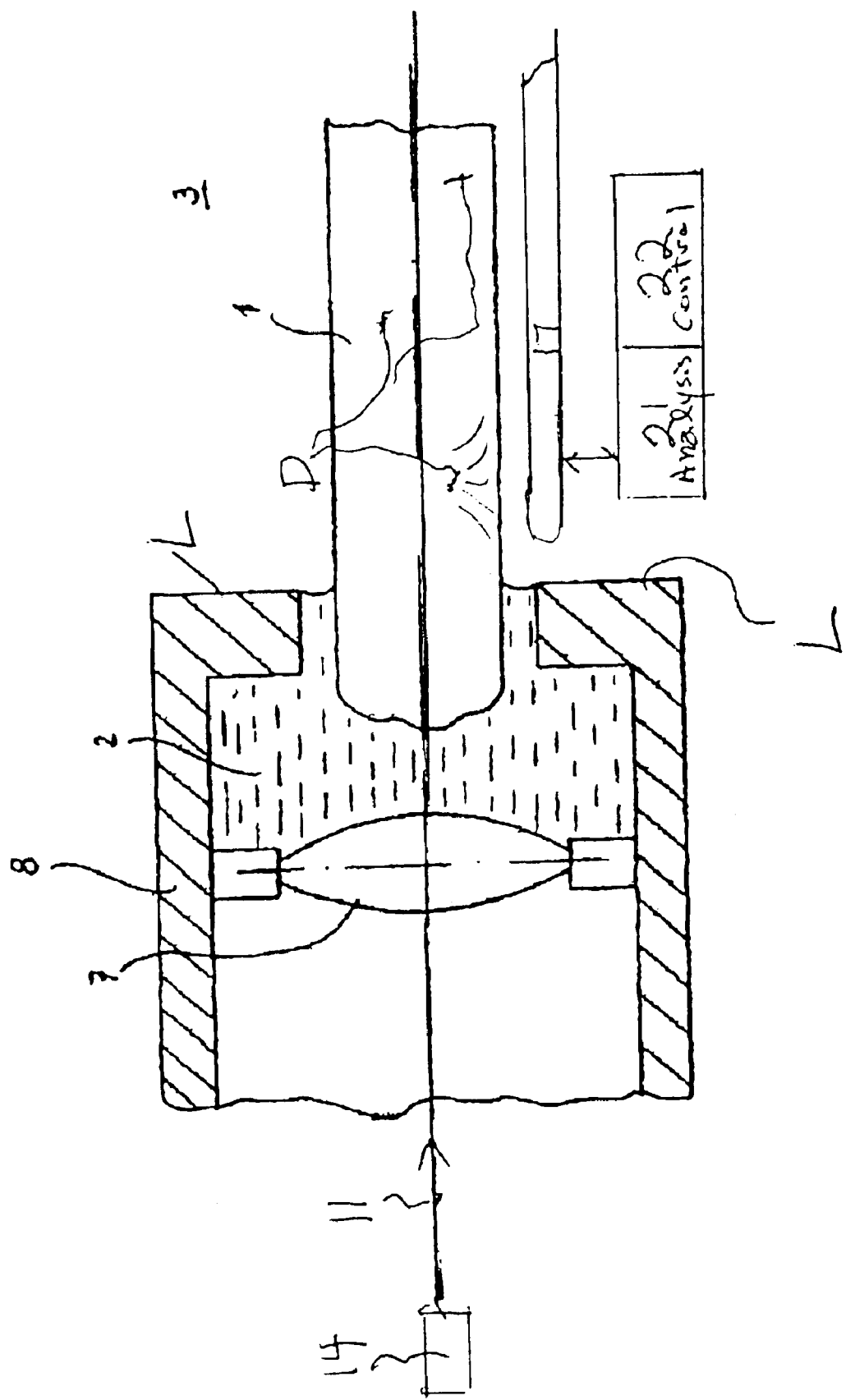

METHOD AND APPARATUS FOR DETECTING DEFECTS IN A CONTINUOUSLY MOVING STRIP OF TRANSPARENT MATERIAL

BACKGROUND OF THE INVENTION

1. Field of the Invention

The present invention relates to a method and apparatus for detecting defects or faults in a continuously moving strip of transparent material, especially a thin glass strip or band, by means of a narrow light beam conducted through the strip transverse to its motion direction, whose scattered light originating from the defect or defects is detected, evaluated and processed to produce a control signal.

2. Description of the Related Art

Testing for faults or defects is of considerable importance in the manufacture of thin glass. Defects with a size of more than 100 Пm are not accepted by the consumers and must thus be reliably detected. To an increasing extent machine testing methods, which are more economical and reliable, are used beside the still conventional visual inspection by trained personnel.

It has been shown that transmitted light methods, in which the strip is passed between a light transmitter and a light receiver, do not meet the requirements at higher strip speeds. These strip speeds reach 10 m/min in modern production plants, in which the exposure time for the measurement is in a range of 150 microseconds. Also limits are placed on the on-line-defect testing by the useable light intensities.

Also it is often overlooked that the test light is introduced edge-wise into the strip and the strip is used as a light guide. The light is reflected repeatedly on the boundary surfaces of the strip with the surrounding atmosphere, as in a glass fiber used as a light guide.

A method of this type, for example, is disclosed in Japanese Patent Publication H 10-339705 of Dec. 22, 1998. According to this reference the defects to be detected in a glass panel continuously moving at about 4 m/min are measured. Light is coupled into both longitudinal edges of the panel and the resulting scattered light originating from the defect or fault is acquired or captured by means of vertical linear sensors arranged above and below the glass. Signals from the linear sensors are processed in an electronic analysis device. In order to exclude uninteresting particles adhering to the surfaces from the defect detection, the light should be introduced inclined to the side edges and conducted further from the outside to the inside by internal reflection at the boundary surface between the glass and the surrounding atmosphere. When using halogen lamps as the light source, that the intensity of the input test light strongly decreases, because of absorption at the center of the strip, for example with a 1.2 m width strip to 5% of the value at the edge, must be considered or taken into account. Thus during analysis an expensive computational compensation is required in order to correctly judge the size of the defects over the entire width of the edge from the acquired scattered light. The known method is limited to certain strip widths and strip speeds, because the required initial intensity of the input test light must be greatly increased with increasing strip width and speed and finally reaches an engineering limit.

In addition the known process presupposes trimmed side edges, because a definite input of the test light is not possible with the rounded edges and uncontrolled production conditions. Because the glass fractures or splits uncontrollably starting from the cut position in a direction opposite from the continuous motion direction and thus produces waste, the trimming of the long edges of the strip is not possible. Thus trimming cannot be used in online testing of a continuously moving strip.

Besides the known method also was not conceived for defect testing in a continuously moving strip, but for glass panels with trimmed long edges and a starting edge and an end edge, which are detected during forward motion by photocells and which are used to produce control signals for starting and stopping the testing process.

SUMMARY OF THE INVENTION

It is an object of the present invention to provide a method and apparatus of the above-described kind, in which the test light can be input to the continuously moving strip of transparent material, without requiring the prior cutting off or trimming of its production-dependent uncontrolled lateral edges.

Furthermore it is another object of the present invention to provide an apparatus and method for detecting material defects >50 Пm in size in a thin glass strip with a thickness in a range of 0.3 to 2 mm and a strip width of at least 2 m at a production speed up to 10 m/sec.

According to the invention a monochromatic light beam is used and is coupled into the strip by means of a transparent liquid arranged between the light source and the strip.

According to a first embodiment of the invention the light beam is coupled into the strip inclined to a surface of the strip and a liquid is used whose index of refraction is larger than that of the atmosphere surrounding the strip, which is normally air. Thus the angle of incidence of the light beam can be selected so that the light is coupled into the upper side of the strip by means of a liquid region bordering the middle of the strip. The light reflected from the lower side of the strip strikes the upper side of the strip or sheet, but on a region, which is outside of the liquid region. Thus this light is reflected back and not coupled out of the strip. In other words, when the light beam is coupled into the transparent material under a sufficiently large angle Δ to the normal to the strip surface across a liquid with a larger index of refraction than that of the surrounding atmosphere, it is possible to make the reflection angle in the strip of material so large that the light reflected at the underside of the strip impinges or strikes on a region of the upper side of the strip outside of the liquid boundary. The light thus is "held captured" in the strip analogous to the total reflection occurring in a light guide. Thus it is guided further transversely to the continuous motion direction of the strip. Tests have shown that the light power that is required for defect detection can be coupled into the strip in this way with the above-described boundary conditions.

According to a second embodiment of the inventive concept the light beam is coupled into the strip parallel to the surface of the strip across its side edges and a liquid is used whose index of refraction substantially corresponds to the index of refraction of the strip of material. The decision for this is based on the knowledge that the difficulties involved in coupling in the test light due to production-conditioned irregularities and rounded side edges can be overcome, when a liquid is arranged between a light source and the strip, which completely fills the space between the light source and the running strip so that the light can be continuously coupled into the side edges of the strip without refraction at the boundary surface between the liquid and the strip.

Further details of the preferred embodiments of the method are described in more detail in the dependent method claims appended hereinbelow.

For example, the light source and the moving strip may be spaced at a predetermined distance from each other so that the transparent liquid is retained in the vicinity of the light beam passing through the transparent liquid by surface tension of the transparent liquid alone. This distance between the light source and the strip may be kept constant by suitable mechanical means, such as rollers or slid members.

To perform the second embodiment of the method the light source may be equipped with a U-shaped guide surrounding the edge side of the moving strip through which the light beam is coupled into the moving strip and the U-shaped guide has legs extending over the top and bottom sides of the moving strip so that the transparent liquid is retained between the U-shaped guide and the moving strip by surface tension of the transparent liquid alone.

Alternatively a sealing device may be used to assist in retaining the transparent liquid. However portions of the transparent liquid carried away by the moving strip may be replenished from a reservoir in both embodiments of the method.

In both embodiments of the method the monochromatic light beam preferably has a wavelength in a range from 400 to 1000 nm. The wavelength is selected within this range so that a minimum amount of monochromatic light is absorbed in the transparent material of the moving strip. It is advantageous when the monochromatic light beam is a weakly convergent laser light beam with a convergence angle such that a focal point of the laser light beam is in the vicinity of an edge of the moving strip opposite another edge into which the light beam is coupled and/or light absorption along a measurement path is minimized.

According to the invention the apparatus for detecting defects in a continuously moving strip of transparent material, especially a thin glass strip, comprises means for continuously conveying the strip of transparent material in a motion direction;

a light source for generating a monochromatic light beam;

a light guide system for guiding the light beam by which the light beam is guided to an edge region of the moving strip;

a transparent liquid arranged between the light source generating the monochromatic light beam and the moving strip so that the light beam is coupled into the moving strip;

a light receiving device for light scattered from the light beam by defects in the moving strip, the light receiving device extending over an entire width of the moving strip in a direction transverse to the motion direction of the moving strip; and means for electronically analyzing the light scattered from the light beam according to size and position of the defects and means for processing the light scattered from the light beam to produce control signals for marking the defects on the moving strip and for controlling devices with which the moving strip is formated according to the defects.

According to a preferred embodiment of the apparatus according to the invention the transparent liquid is arranged between an edge side surface of the moving strip and a stationary end part of the light guide system, which extends parallel to surfaces of the moving strip. In this embodiment the transparent liquid has an index of refraction greater than that of an atmosphere surrounding the moving strip. It also includes a prism and the transparent liquid is arranged between the prism and the edge side surface of the moving strip.

A second preferred embodiment of the apparatus according to the invention includes a U-shaped guide embracing the edge region of the moving strip, and the transparent liquid is arranged between the moving strip and the U-shaped guide, whose legs embrace an end part of the light guide system. In this embodiment the transparent liquid has an index of refraction about equal to that of the transparent material of the moving strip. The light beam is coupled into the moving strip through an edge surface of the moving strip.

BRIEF DESCRIPTION OF THE SEVERAL VIEWS OF THE DRAWING

The objects, features and advantages of the invention will now be illustrated in more detail with the aid of the following description of the preferred embodiments, with reference to the accompanying figures in which:

FIG. 2 is a cutaway sectional view of the coupled-in region according to FIG. 1 showing features of the apparatus according to the invention; and FIG. 3 is a schematic cross-sectional view of the coupled-in region for coupling light into the side edges of a strip of transparent material according to a second embodiment of the method according to the invention.

DETAILED DESCRIPTION OF THE INVENTION

Figure 1A:
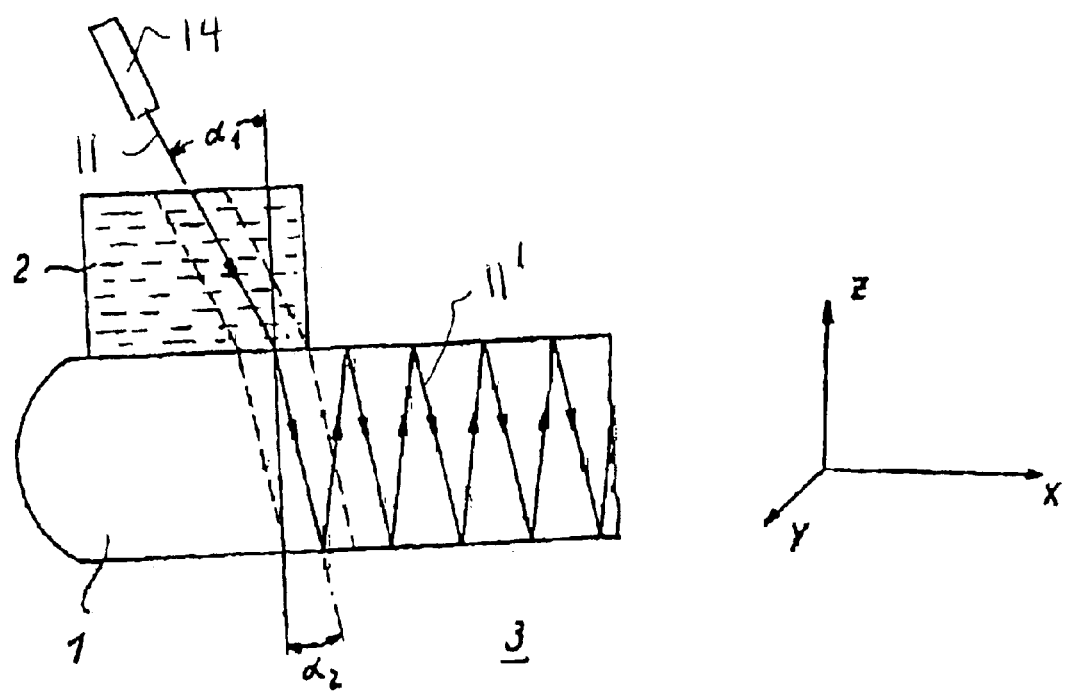
FIGS. 1a and 1b are diagrammatic sectional views, illustrating the principle for coupling light into a strip of transparent material according to a first embodiment of the invention.
Figure 1B:
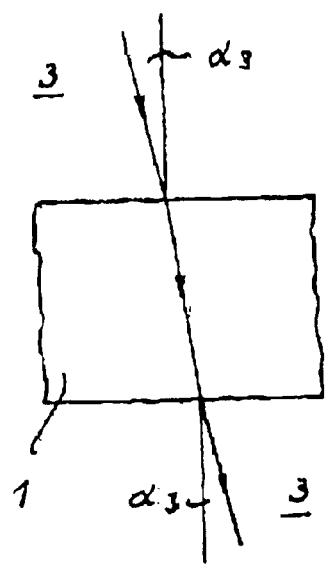

In FIGS. 1a and 1b the edge region of a glass strip 1 to be tested is shown, which moves continuously perpendicular to the plane of the drawing, i.e. in the direction of the Y-axis with the production speed. The X-axis extends transversely to the motion direction in the direction of the strip width, while the Z-axis extends perpendicular to the upper surface of the strip. Accordingly the defect or fault positions to be detected are located according to the coordinate system shown in FIG. 1a and are processed for production of control signals.

A transparent liquid 2 is arranged between the end of an incompletely shown light guide system (FIGS. 2, 3) and the upper surface of the moving glass strip 1, whose index of refraction $\alpha_1$ is greater than the index of refraction $\alpha_3$ of the surrounding atmosphere 3, which is usually air. The monochromatic light beam 11 from a laser 14 is coupled into the glass strip 1 with an index of refraction $\alpha_2$ through the liquid 2. The light beam 11 is defracted toward the perpendicular to the glass surface and reflected at the lower boundary surface between glass and air, as shown in FIG. 1a. The part of the light beam 11', which reaches the upper boundary surface (glass/air) beyond the part contacted by the liquid, does not emerge or pass out of the glass strip 1, but is again reflected and subsequently is guided further in the X-direction to the opposite edge of the glass strip 1 by repeated reflections. Thus the glass strip 1 acts as a light guide, in which the light beam 11 remains captured on account of internal reflection at the upper and lower boundary surface between glass and air. In this way the test light can be coupled into the glass strip at the lateral edge regions for defect or fault detection or measurement, without further processing of the production-dependent irregular edge surfaces.

If light is coupled into the glass strip 1 through a medium (air), which is also located under the glass strip, the light beam 11 coupled into the strip is not reflected at the lower boundary surface, but completely passes out of the strip, as shown in FIG. 1*b*.

It is apparent from the cutaway view in FIG. 2 that the glass strip or sheet 1 is conveyed or supported on rolls 6 or the like. The light guide system 5 includes a prism 4 with a surface parallel to the upper surface of the glass strip 1. A transparent liquid 2 is arranged between the prism 4 and the glass strip 1 according to the invention, which has a greater index of refraction than the surrounding (air) atmosphere 3. The liquid 2 has a certain surface tension, by means of which it is held between the stationary prism 4 and the glass strip 1 moving perpendicular to the plane of the drawing. In so far as it is required also sealing means can be provided sliding or rubbing on the glass strip. The edges of the glass strip are cut away and thrown out during shaping so that scratches caused by foreign bodies on the glass strip are unimportant.

In the alternative embodiment shown in FIG. 3 the monochromatic light beam 11 from the laser 14 is coupled into the glass strip 1 parallel to its upper surface through the unworked edge surface. Also a U-shaped guide 8 is provided, in which the end portion of a light guide system, in this case a lens 7 is mounted. The guide 8 embraces the edge region of the glass strip 1 with legs L and encloses a liquid 2, which has about the same index of refraction as the glass of the glass strip. Because of that no light refraction occurs at the irregularly formed liquid/glass boundary surface so that the test light can be coupled practically loss-free into the glass strip in a direction transverse to its motion direction. Also the glass strip acts as a light guide here. No light can escape from it into the surrounding atmosphere (air).

The liquid 2 is again kept in the stationary guide 8 because of surface tension. Understandably also seals can be provided in addition.

Other features of the apparatus of the invention are also shown in FIG. 3. A light-receiving device 17 detects light scattered from the light beam 11 by defects D in the glass strip. The light-receiving device 17 produces electronic signals containing information regarding size and position of the defects, which are input into an electronic analysis device 21 coupled with a control device 22. The analysis device 21 processes the electronic signals from the light-receiving device 17 and the control device 22 produces signals for marking the defects and or controlling formatting of the continuously moving strip during subsequent working operations.

Finally in both embodiments it can be provided that amounts of the transparent liquid 2 conducted away from the apparatus by the moving glass strip can be replaced by liquid from a reservoir.

The disclosure in German Patent Application 102 21 945.1 of May 13, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method and apparatus for detecting a defect or defects in a continuously traveling strip or band of transparent material, especially glass, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of detecting defects in a continuously moving strip of transparent material, said method comprising the steps of:
   a) conducting a monochromatic light beam through said continuously moving strip transverse to a motion direction of the moving strip;
   b) coupling the monochromatic light beam into the continuously moving strip by a transparent liquid, said transparent liquid being arranged between a light source generating said monochromatic light beam and said continuously moving strip so that the light beam passes through the transparent liquid into the moving strip;
   c) detecting light scattered from the monochromatic light beam by defects present in the moving strip; and
   d) evaluating said light scattered from the monochromatic light beam in step c) and processing said light scattered from the monochromatic light beam to produce a control signal.

2. The method as defined in claim 1, wherein said monochromatic light beam is coupled into said continuously moving strip of said transparent material through an edge region of said continuously moving strip.

3. The method as defined in claim 2, wherein said monochromatic light beam is inclined to an upper surface of said continuously moving strip through which said monochromatic light beam passes.

4. The method as defined in claim 3, wherein said transparent liquid has an index of refraction that is greater than that of an atmosphere surrounding said continuously moving strip.

5. The method as defined in claim 4, wherein said light source and said continuously moving strip are spaced a distance from each other such that the transparent liquid is retained in the vicinity of the light beam passing through the transparent liquid by surface tension of said transparent liquid alone.

6. The method as defined in claim 5, wherein said distance between said light source and said continuously moving strip is kept constant by suitable mechanical means.

7. The method as defined in claim 6, wherein said light source is supported by rollers or slide pieces on said moving strip and said moving strip rests on rolls.

8. The method as defined in claim 2, wherein said light beam propagates in a direction parallel to an upper surface of said continuously moving strip and passes through an edge surface of said continuously moving strip in said edge region.

9. The method as defined in claim 8, wherein said transparent liquid has an index of refraction that is about equal to that of the transparent material of said continuously moving strip.

10. The method as defined in claim 9, wherein said light source is equipped with a U-shaped guide embracing said edge region of the continuously moving strip, said U-shaped guide has legs and said legs are spaced from a top side and bottom side of said continuously moving strip so that said transparent liquid is retained between said U-shaped guide and said continuously moving strip by surface tension of said transparent liquid alone.

11. The method as defined in claim 10, further comprising providing a sealing device between said U-shaped guide and said continuously moving strip for additional sealing of said transparent liquid between said U-shaped guide and said continuously moving strip.

12. The method as defined in claim 10, further comprising replacing portions of said transparent liquid carried off by motion of the continuously moving strip relative to the light source by other portions of said transparent liquid from a reservoir.

13. The method as defined in claim 10, further comprising mechanically positioning said moving strip between the legs of the U-shaped guide by a mechanical device.

14. The method as defined in claim 13, wherein said mechanical device comprises rolls or slid members.

15. The method as defined in claim 5, further comprising providing a sealing device between said moving strip and said light source for further sealing to additionally help retain said transparent liquid between said light source and said moving strip.

16. The method as defined in claim 5, further comprising replacing portions of said transparent liquid carried off by motion of the moving strip relative to the light source by other portions of said transparent liquid from a reservoir.

17. The method as defined in claim 1, wherein said monochromatic light beam consists of monochromatic light having a wavelength in a range from 400 to 1000 nm.

18. The method as defined in claim 17, wherein said wavelength is selected so that a minimum amount of said monochromatic light is absorbed in said transparent material of said moving strip.

19. The method as defined in claim 1, wherein said monochromatic light beam is a weakly convergent laser light beam.

20. The method as defined in claim 19, further comprising selecting a convergence of said weakly convergent laser light beam, so that light absorption along a measurement path is compensated and/or a focal point of said laser light beam is in the vicinity of an edge of said moving strip opposite another edge into which said light beam is coupled.

21. The method as defined in claim 1, wherein said light beam has a width of from 0.5 to 3 mm at a point where said light beam is coupled into said moving strip, as measured in said motion direction of said moving strip.

22. The method as defined in claim 1, further comprising providing a window for scattered light observation having a width in a range of 10 Πm, as measured in said motion direction of said moving strip.

23. The method as defined in claim 1, wherein said evaluating comprises electronically analyzing said light scattered from the light beam in regard to intensity and defect location and said processing said light scattered from the light beam comprises producing at least one of a marking signal for defect marking and a cutting signal for control of a cutting device.

24. The method as defined in claim 1, further comprising compensating light absorption occurring across an entire width of said continuously moving strip during processing of said light scattered from the light beam, as needed.

25. The method as defined in claim 1, wherein said continuously moving strip of transparent material is a thin glass strip.

26. An apparatus for detecting defects in a continuously moving strip of transparent material, especially a thin glass strip, said apparatus comprising
means for continuously conveying the strip of the transparent material in a motion direction;
a light source for generating a monochromatic light beam;
a light guide system for guiding the monochromatic light beam to an edge region of the continuously moving strip;
a transparent liquid arranged between said light source generating said monochromatic light beam and said moving strip so that the monochromatic light beam is coupled into the continuously moving strip;
a light receiving device for light scattered from the monochromatic light beam by defects in the continuously moving strip, said light receiving device extending over an entire width of the continuously moving strip in a direction transverse to the motion direction of the continuously moving strip; and
means for electronically analyzing said light scattered from the light beam according to size and position of said defects and means for processing said light scattered from the light beam to produce control signals for marking said defects on said continuously moving strip and for controlling devices with which the continuously moving strip is formated according to said defects.

27. The apparatus as defined in claim 26, wherein said transparent liquid is arranged between an edge side of an upper surface of the continuously moving strip and a stationary end part of the light guide system, said stationary end part extending parallel to said upper surface of the continuously moving strip, and wherein the transparent liquid has an index of refraction greater than that of an atmosphere surrounding the moving strip.

28. The apparatus as defined in claim 27, further comprising a prism and wherein said transparent liquid is arranged between said prism and said edge side of said upper surface of the continuously moving strip.

29. The apparatus as defined in claim 28, further comprising means for maintaining said stationary end part at a predetermined distance from said continuously moving strip, said means for maintaining comprising rollers or slid members.

30. The apparatus as defined in claim 26, further comprising a U-shaped guide embracing said edge region of said continuously moving strip, and wherein the transparent liquid is arranged between the continuously moving strip and the U-shaped guide, the end part of the light guide system is positioned in the U-shaped guide, the transparent liquid has an index of refraction that is about equal to that of the transparent material of the continuously moving strip and the light beam is coupled into said edge region of the continuously moving strip parallel to an upper surface of the continuously moving strip.

31. The apparatus as defined in claim 30, wherein said U-shaped guide has a leg extending above the moving strip and another leg extending below the moving strip and is kept at a predetermined distance from said moving strip by means of rollers or slid members.

32. The apparatus as defined in claim 26, further comprising a liquid reservoir for replenishing said transparent liquid, as required.

* * * * *